(12) United States Patent
Derrieu et al.

(10) Patent No.: US 6,500,446 B1
(45) Date of Patent: Dec. 31, 2002

(54) COMPOSITIONS WHICH CONTAIN AT LEAST ONE CATIONIC POLYMER AND AT LEAST ONE ACTIVE MOLECULE CONTAINED IN AT LEAST ONE MICRO OR NONOPARTCULATE VECTOR, AND THEIR USE FOR TREATING LIVING OR INERT SURFACES

(75) Inventors: Guy Derrieu, Cagnes sur Mer; Jean-Luc Pougnas, Saint Laurent du Var; Patricia Monginoux, Nice; Christian Karst, Villeneuve Loubet, all of (FR)

(73) Assignee: Virbac, Carros (FR)

( * ) Notice: Subject to any disclaimer, the term of this patent is extended or adjusted under 35 U.S.C. 154(b) by 0 days.

(21) Appl. No.: 09/059,200

(22) Filed: Apr. 14, 1998

(30) Foreign Application Priority Data

Apr. 14, 1997 (FR) .............................. 97 04549

(51) Int. Cl.$^7$ .............................. A01N 25/28
(52) U.S. Cl. ................ 424/408; 424/401; 424/405; 424/406; 424/450; 424/78.02; 424/78.03; 523/122

(58) Field of Search ............................ 523/122; 514/55; 424/401, 405, 406, 408, 450, 78.02, 78.03, 78.06, 78.07

(56) References Cited

U.S. PATENT DOCUMENTS

| | | | |
|---|---|---|---|
| 4,617,186 A | | 10/1986 | Schafer et al. |
| 4,855,090 A | | 8/1989 | Wallach |
| 5,464,629 A | | 11/1995 | Monshipouri et al. |
| 5,610,201 A | | 3/1997 | Grollier et al. |
| 5,696,098 A | * | 12/1997 | Muraki ..................... 514/55 |
| 5,779,471 A | * | 7/1998 | Tseng et al. .................. 433/80 |

FOREIGN PATENT DOCUMENTS

| | | |
|---|---|---|
| EP | 0373988 | 6/1990 |
| WO | 96/12469 | 5/1996 |

\* cited by examiner

*Primary Examiner*—Neil S. Levy
(74) *Attorney, Agent, or Firm*—Dennison, Schultz & Dougherty

(57) ABSTRACT

The present invention relates to compositions which contain at least one cationic polymer and at least one active molecule contained in at least one micro or nanoparticulate vector, and their use for treating living or inert surfaces.

17 Claims, No Drawings

COMPOSITIONS WHICH CONTAIN AT LEAST ONE CATIONIC POLYMER AND AT LEAST ONE ACTIVE MOLECULE CONTAINED IN AT LEAST ONE MICRO OR NONOPARTCULATE VECTOR, AND THEIR USE FOR TREATING LIVING OR INERT SURFACES

BACKGROUND OF THE INVENTION

The invention relates to compositions for improving the activity or intrinsic activity (activities) of an active molecule by persistence and maintenance (or increase) of this (these) activity (activities), for long periods of time, said compositions being used by application onto living or inert surfaces.

These compositions are usable for example in the fields of human or veterinary medicine, especially in dermatology or cosmetics; in human or veterinary hygiene; in domestic products; in products for use in the environment, especially such as plant treatment products (in particular treatment of their aerial part), and in the fight against insects.

These compositions comprise at least one cationic polymer and at least one active molecule contained in at least one micro or nanoparticulate vector.

Several families of products are known in dermatology and in cosmetology which are presented in many forms and which are used by application onto the skin or the hair in man, and onto the skin and hair of animals, which act:

to wash with rinsing, for example shampoos, liquid soaps, syndets (synthetic detergents), to clean without rinsing, for example dry shampoos, milks, lotions, to treat or to embellish, for example lotions, gels, milks, creams, ointments, pressurised or mechanical sprays, sticks.

In every case, these products must bring about, after their use, with or without rinsing, a beneficial embellishing and/or treating action. Hitherto, every preparation has a cosmetic or dermatological activity which appears just after the treatment, but without persistence with time.

Domestic or environmental products are also known which are presented in many forms, solutions or suspensions, creams, gels, pressurised or mechanical sprays, which have various uses such as, for example:

the cleaning of surfaces, objects or linen (detergent products), the embellishment of surfaces, optionally plant surfaces (polishing or glossing products), the pest control of premises or plants, with, amongst others, adherence on insects, the disinfection of surfaces, plant protection products.

Furthermore, in order to maintain the activity over a long period of time, it is necessary to increase the amounts of active molecules which in many cases leads to the acceptability threshold being surpassed:

in dermatology and cosmetology, skin problems are observed, i.e. the appearance of adverse reactions, irritations, redness, itching, lesions;

in hygiene and during a use in the environment, problems of inconvenience for the living beings present during the use or after the use of the product, a degradation of the surfaces, or bums for the plants, are observed for example.

Such a increase also leads to technical difficulties in introducing these large amounts of active molecules into the formulations.

Compositions having treating and/or embellishing actions have now been developed for these types of products which last over long periods of time so as to prevent the repetition of the applications, (this repetition causing harmful effects while maintaining a treating cover), in particular without a break between the applications recommended in the regimen of use.

SUMMARY OF THE INVENTION

The invention therefore relates to compositions which comprise at least one cationic polymer and at least one active molecule contained in at least one micro or nanoparticulate vector, by virtue of which compositions the drawbacks described above as far as the persistence of the activity is concerned may be avoided.

In the rest of the description, the term <<polymer>> comprises homopolymers as well as copolymers.

In a surprising way, the combination of at least one cationic polymer and at least one active molecule in a micro or nanoparticulate vector gives rise to a synergy between said polymer and the micro or nanoparticles which enables not having to increase the amounts of actives, while maintaining the activity over a long period of time.

In particular, this synergistic effect is observed on the surface of the skin and at the contact with the hair over longer periods of time than those provided by existing vectorial systems, without having to increase the amount of the actives.

Further, it has been established that the choice of the micro or nanoparticulate vector, of the cationic polymer, and more exactly, the combination of the two could modulate the activity of the composition; each combination must of course be the subject of particular studies in order to determine the amounts of actives to be used in the vectors, and in order to determine the period of activity.

These compositions are stable in storage, and present excellent treating and/or embellishing properties. They are also better tolerated and have a better harmlessness vis-à-vis the skin, the hair and the eyes in cosmetology and dermatology, as well as vis-à-vis the environment.

DETAILED DESCRIPTION OF THE INVENTION

The compositions according to the invention are characterised by the fact that they comprise, in a medium acceptable for a pharmaceutical use, in particular a dermatological, veterinary, cosmetic, or hygiene use, or for domestic applications or applications in the environment:

a) 0.001 to 5%, by weight of the total weight of the composition, of a cationic polymer, or of a mixture of cationic polymers;

b) 0.5 to 50%, by weight of the total weight of the microparticle composition or nanoparticle composition which contain one or more active molecules.

The compositions according to the invention can be used in any application set forth above, and in particular for a topical pharmaceutical or veterinary treatment of human skin or hair, or of animal skin or hair, or for eliminating parasites.

The cationic polymers used in accordance with the present invention, are selected for example from:

quaternised polymers or copolymers, such as, for example, quaternised derivatives of polyvinylpyrrolidone (PVP); quaternised copolymers of PVP and hydrophilic polymers (urethane, acrylate, etc.), in particular the copolymers of PVP, dimethylaminoethylmethacrylate and polyurethane (marketed under the name Aquamere C by the company Hydromer Inc.);

ammonium salts of synthetic polymers or copolymers known under the designation "Polyquaternium" such as described in the International Cosmetic Ingredient Dictionary published by the <<Cosmetic, Toiletry and Fragance Association>>, (C.T.F.A.);

cationic silicones;

cationic polysaccharides of natural, biotechnological or synthetic origin, naturally cationic or quaternised, such as, for example, modified guar gums, chitosan or modified chitosans and their salts; celluloses, modified celluloses and their derivatives, such as, for example, sodium carboxymethylcellulose; chitin derivatives;

polyamine derivatives, optionally substituted with polyethylene glycol chains;

polyaminoacids under pH conditions in which they are cationic;

polyethyleneimine.

Preferably, from the cationic polysaccharide family, chitosan and its derivatives will be used. Chitosan is a polyglucosamine which is obtained by deacetylation of chitin, several uses of which have been proposed in cosmetology and dermatology. In the case of aqueous solutions, chitosan is used in particular in the form of its soluble salts with organic acids or anionic surfactants.

The polysaccharides are defined in greater detail in numerous books. The book by R. A. A. Muzzarelli, "The Polysaccharides", (1985) Academic-Press, may be referred to in particular.

In a preferred aspect, the polysaccharides usable according to the invention can be selected from chitosan or modified chitosans such as N-acyl chitosans, N-carboxyalkyl chitosans, N-carboxyacyl chitosans, O-carboxyalkyl chitosans, deoxyglycit-1-yl chitosans, hydroxyalkyl chitosans, or salts thereof.

More particularly, the pyrrolidone carboxylic acid salt of chitosan (chitosan PCA), the glycolic acid salt of chitosan (chitosan glycolate), the lactic acid salt of chitosan (chitosan lactate), the monosuccinamide of chitosan (chitosan monosuccinamide or chitosanide) will be used for example.

Other preferred cationic polymers are quaternised guar gums such as guar hydroxypropyltriammonium chloride or the hydroxypropyl derivative thereof (marketed under the names Jaguar C13S and Jaguar C162 respectively by Rhône Poulenc).

As micro or nanoparticulate vector, any colloidal system can be used which has been the subject of numerous researches which have given rise to new technologies being the subject of patents or publications.

As non-limiting examples, microcapsules, microspheres, macromolecular complexes, nanospheres, nanocapsules, latexes or vesicles can be cited.

The following may especially be used liposomes;

paucilamellar lipidic vesicles prepared according to the U.S. Pat. No. 4,855,090 and designated Novasomes®: these vesicles are prepared by a method in which a lipophilic phase is prepared by mixing a surfactant agent with a sterol and a charge producing amphiphile agent while at the same time maintaining the temperature above the melting point of this surfactant agent, followed by mixing the amphiphilic material to be encapsulated with this lipophilic phase approximately spherical multilamellar vesicles of onion structure described in the application WO 93/19735 designated Spherulites®: these vesicles are obtained by a method in which a liquid crystal homogeneous lamellar phase is prepared which comprises at least one surfactant and at least one solvent and, if need be, a substance which is to be encapsulated and which forms a stacking of membranes, and in which this lamellar phase is subjected to a constant shearing. This method allows vesicles of controlled sizes to be obtained, not only from lipidic surfactants which can form liposomes, but also from the various anionic and nonionic surfactants;

microcapsules based on polyurethane, polyurea resin, polyamide resin, polyamide-polyurea resin, polycarbonate resin, polysulphonate resin, polysulphonamide resin or epoxy resin such as described in the patent FR 2 595 545.

Preferably, the nano or microparticulate vectors usable in the compositions according to the invention have a diameter between 0.01 and 150 μm, preferably between 0.1 and 0.5 μm for the nanoparticulate vectors and between 1 and 50 μm for the microparticulate vectors.

The choice of the nature of the micro or nanoparticles, the constituents of their structure, and also the technology employed is firstly a function of the nature of the active molecules considered and of the form desired for the use in dermatology or cosmetology, or for domestic applications or applications in the environment.

In particular, the technology which enables obtaining multilamellar vesicles of onion structure(i.e. where the bipolar membranes are present up to the core of the vesicle), Spherulites®, namely the homogeneous shearing of a lamellar liquid crystal phase such as described in the application WO 93/19735, can include aqueous media as well as organic media, i.e. alcoholic, glycolic, lipidic media, or their mixtures, which allows an acceptability for all those in the fields considered. Similarly, the technology allows multilamellar vesicles to be prepared which include any active molecule whatever their physical state: liquid or solid.

Some of these technologies, in particular the technology which allows multilamellar vesicles to be obtained, enable combining a polymer with the structure of said vesicles, which confers to them various specific characters according to the polymer used, such as the regulation of the release of the active molecule(s), the increase of the stability of the vectors, the increase in the adhesion to the surfaces, in particular the skin, or the hair.

In an advantageous aspect, the micro or nanoparticulate vectors usable in the compositions according to the invention comprise one or more cationic polymers in their structure. Preferably, said vectors containing in their structure one or more cationic polymers are multilamellar vesicles of onion structure or Spherulites® such as defined above. Advantageously, the cationic polymer is in this case a polysaccharide derivative, preferably a cationic chitosari derivative or a guar gum.

In another advantageous aspect of the invention, the active molecule(s) is (are) contained not only in the micro or nanoparticulate vectors, but also in the excipient phase of the final formulation.

"Active molecules", contained in the micro or nanoparticulate vectors of the compositions according to the invention, is understood as meaning any molecule or chemical composition, such as a natural product originating from the plant, animal or mineral kingdom, or a synthetic product, which has any pharmaceutical, biological, dermatological, cosmetic, or domestic activity or an activity upon the environment, including plants and insects.

The following may especially be cited:
hydrosoluble molecules (extracts of algae, vitamins, hydrosoluble proteins, protein hydrolysates, peptides, α-hydroxyacids, salicylic acid, caffeine derivatives, . . . );
liposoluble molecules (vegetable and animal oils, carbon or silicone synthetic oils, essential oils and their mixtures, perfumes and aromas, vitamins, fatty acid derivatives . . . ).

"Molecule having a biological activity", is understood as meaning especially, in an non-limiting manner, any molecule having a prophylactic or curative biological activity, in vitro or in vivo, especially an anti-infectious agent, in particular an antiseptic, antibiotic, antiviral, antifungal, antiparasitic agent, especially an insecticide or acaricide, or antimitotic agent.

In an advantageous aspect, the compositions according to the invention can comprise several active molecules combined in one or more types of microparticulate or nanoparticulate vectors.

Of course, care will be taken in selecting a formulation adapted to the formed desired such that the advantageous properties intrinsically attached to the binary combination according to the invention shall not be altered by the formulation.

The compositions according to the invention can be presented in a liquid, paste or solid form by using the usual additives according to the application considered, for example preservatives, stabilisers, perfumes, softeners, moisturisers, thickeners.

The compositions according to the invention are obtained by mixing the phase containing the micro or nanoparticulate vectors which contain the active molecule(s) such as obtained at the end of their preparation, for example in the dry form or in suspension, or after dispersion in the medium selected in function of the application considered, with the phase which contains the cationic polymer(s) as well as the additives usually used according to the application sought after and which can optionally contain one or more active molecules as well.

The invention also relates to a method of treating an animal or plant living surface, or an inert surface, which consists in applying a composition according to the invention onto said surface. Notably, said surface is a living surface such as the skin, the hair, or the integuments of a human being; the skin, the hair or the integuments of an animal; the cuticle of plants or insects.

In another aspect, said surface is an inert surface such as a natural or synthetic fibre, or a collection of fibres, such as a tissue.

In particular, the method according to the invention consists in applying said composition onto a surface in the presence of water, and in carrying out one or more rinses with water of said surface, without the intrinsic activity of said composition being eliminated.

In another particular aspect of said method, the composition is applied onto a surface and said surface is wiped to remove dirty marks, without the intrinsic activity of said composition being eliminated.

The invention also covers in one of its aspects a method of therapeutic, cosmetic, or hygiene treatment of the human or animal body by the application of a composition such as described above.

According to one of its aspects, the invention also relates to the use of a composition such as defined above for the preparation of a pharmaceutical, veterinary, cosmetic formulation, or animal or human hygiene formulation, or a formulation for the treatment of plants or for the destruction of insects.

Another object of the invention is a method for improving the intrinsic activity (activities) of one or more active molecule(s) by persistence and increase of this (these) activity (activities) which consists in combining, within a composition such as defined above, said active molecule(s) contained in one or more types of microparticles or nanoparticles with one or more cationic polymers.

The Examples that follow are intended to illustrate the invention without limiting the scope thereof.

EXAMPLE 1

Hypoallergenic foaming solutions for dogs are prepared which are of emollient character having the following formulae expressed in percentage m/m:

| FORMULA | A | B | C |
| --- | --- | --- | --- |
| Lauramide DEA | 10.30 | 10.30 | 10.30 |
| TEA-Lauryl Sulphate | 7.15 | 7.15 | 7.15 |
| Urea | 5.00 | 6.00 | 5.00 |
| Spherulite ®* | 5.00 | 0 | 5.00 |
| Chitosanide (1%) | 0.10 | 0.10 | 0 |
| Glycerine | 1.00 | 1.10 | 1.00 |
| Imidazolidinyl Urea | 1.00 | 1.00 | 1.00 |
| Perfume | 1.00 | 1.00 | 1.00 |
| Water | 69.45 | 73.35 | 69.55 |

*the Spherulites ® or multilamellar vesicles of onion structure were prepared according to applications WO93/19735 and WO95/18601 in a medium containing, in m/m, 20% urea, 2% glycerine, and 0.05% chitosanide.

The amounts of active molecules in formula B (urea and glycerine) were increased in order to be identical to the amounts of actives in formulae A and C.

Three groups of six dogs of any race which belong to persons were treated and followed by veterinary surgeons:
the first group with preparation A in accordance with the invention,
the second group with preparation B without Spherulites®, and,
the third group with preparation C without chitosanide.
Various parameters were studied:
cosmetic acceptability and effectiveness, and,
moisturisation of the skin for 28 days by corneometry.

The three formulations showed an equivalent washing action, but only the first and second groups had beautiful, shiny hair after drying which was easy to brush; the coats of these two groups had kept this aspect for a fortnight which demonstrates the effect of the cationic polymer.

Similarly, the moisturisation level was equivalent for the three groups 12 hours after the use of the foaming solutions. A large decrease in the moisturisation was noted on the third day for the second and third groups compared to the first group. A sufficient level of moisturisation was maintained for 12 days which demonstrates the synergy of the combination of the two components of the invention.

Furthermore, the following results were observed by sweeping electronic microscopy on samples of hair on the animals from the first and third groups, before treatment, just after the treatment, the fourth day and the tenth day after the treatment:
1. hair before treatment show dust and debris characteristic of an animal living outside, 2. hair treated with formulation A, immediate observation after air drying, clearly show the Spherulites® bound to them in the form of bunches by the cationic polymer,
3. hair treated with formulation A, observation after 4 days, still show the Spherulites® bound to them by the cationic polymer,
4. hair treated with formulation A, observation after 10 days, show the Spherulites® which are more difficult to observe due to the presence of a lot of debris and dirty marks, a normal situation for an animal having lived outside,
5. hair treated with formulation C, immediate observation, after air drying, clearly show the individualised and very dispersed Spherulites® bound to them,
6. hair treated with the formulation C, observation after 4 days, no longer showing the Spherulites®.

EXAMPLE 2

A softening and soothing lotion is prepared for the skin, for human use, which has the following formula expressed in percentage m/m:

| Formula: | |
|---|---|
| Octyl stearate | 8.00 |
| Emulgade ® SE* | 6.00 |
| Novasomes ®** | 10.00 |
| Glycerine | 5.00 |
| Decyl oleate | 4.00 |
| Cetearylic alcohol | 1.50 |
| Chitosan glycolate | 0.15 |
| Phenylethyl alcohol | 0.20 |
| Water | 69.15 |

*Emulgade ® SE: mixture of glyceryl stearate, ceteareth-20, ceteareth-12, cetearyl alcohol and cetyl palmitate marketed by the company HENKEL.
**Novasomes ® were prepared according to U.S. Pat. No. 4,855,090 in a medium containing, in m/m, 10% Hamamelis extract and 8% menthol.

EXAMPLE 3

A cleansing and cerulytic auricular lotion is prepared, for household animals, dogs and cats, of formulae expressed in percentage m/m:

| FORMULA | A | B |
|---|---|---|
| Monopropylene Glycol | 35.00 | 35.00 |
| Spherulites ®* | 8.00 | 0 |
| Lactic acid | 2.50 | 3.78 |
| Chitosanide (1%) | 0.10 | 0.10 |
| Salicylic acid | 0.10 | 0.42 |
| Chloroxylenol | 0.10 | 0.10 |
| Perfume | 0.01 | 0.01 |
| Colorant FD & C No. 1 | $0.03 \cdot 10^{-3}$ | $0.03 \cdot 10^{-3}$ |
| Water | 54.19 | 60.59 |

*the Spherulites ® were prepared according to the applications WO93/19735 and WO95/18601 in a medium containing, in m/m, 16% lactic acid, 4% salicylic acid, and 0.05% chitosanide.

The amounts of actives in formula B (lactic acid and salicylic acid) were increased in order to be identical with the amounts of actives in formula A.

Two groups of six dogs of any race belonging to persons were treated and followed by veterinary surgeons:
the first group with preparation A in accordance with the invention, and,
the second group with preparation B without Spherulites®.

Various parameters were studied:
pathological and functional signs, and,
evaluation of the amount of cerumen for 14 days by clinical observation.

The two formulations showed equivalent pathological and functional signs, but only the dogs of the first group showed auditory canals which were free from cerumen for 8 days, compared to the dogs of the second group which had the canals blocked with dirt and cerumen after only 48 hours.

EXAMPLE 4

An anti-acarian mechanical spray for the environment is prepared of formula expressed in percentage m/m:

| FORMULA | A |
|---|---|
| Amitraz* microcapsules suspension | 10.00 |
| Aquamere C** | 0.30 |
| Benzyl alcohol | 1.00 |
| Water | 88.70 |

*The suspension of microparticles was carried out by interfacial coacervation according to the method described in the applications EP 0 267 150 and FR 2 595 545 in a medium containing, in m/m, 5% Amitraz(Agr Evo).
**Copolymer of PVP/Dimethylaminoethylmethacrylate/Polycarbamyl polyglycol ester (HYDROMER Inc).

EXAMPLE 5

A depigmenting cream is prepared for eliminating brown marks appearing on the face, the neck or on the arms, having the following formula expressed in percentage m/m:

| FORMULA | A |
|---|---|
| Cutina CBS* | 14.00 |
| Pidobenzone**microspheres | 15.00 |
| Cetearyl octanoate | 2.50 |
| Jaguar C162*** | |
| polpyoxyethylene cetylstearylic-20 alcohol | 1.50 |
| polpyoxyethylene cetylstearylic-12 alcohol | 1.50 |
| Imidazolidinyl Urea | 0.30 |
| Benzophen-3-one | 1.00 |
| Methyl-4-benzylidene camphor | 1.00 |
| methylparaben | 0.20 |
| Propylparaben | 0.10 |
| Water | 62.9 |

*Mixture of monoglycerides/diglycerides, fatty acids, triglycerides, waxy esters (HENKEL).
**Microspheres were prepared by the "spray cooling" technique in a lipidic medium (beeswax) containing, in m/m, 25% Pidobenzone (VIRBAC).
***Guar hydroxypropyltriammonium chloride (RHONE POULENC).

What is claimed is:
1. A composition for skin treatment, comprising:
   a) a pharmaceutically or cosmetically acceptable medium
   b) dispersed directly within the medium, 0.001 to 5% by weight of the composition of at least one cationic polymer selected from the group consisting of cationic polysaccharides; and
   c) dispersed within the medium, 0.5 to 50% by weight of the composition of microparticles or nanoparticles containing at least one biologically active molecule therein selected from the group consisting of an antiseptic, an antibiotic, an antiviral, an antifungal, an antiparasitic, an insecticidal, an acaricidal and an antimitotic for treating the skin, said microparticles or nanoparticles being approximately spherical multilamellar vesicles of onion structure, whereby the combination of the at least one cationic polymer and the microparticles or nanoparticles improves the activity of the at least one active molecule.

2. The composition according to claim 1, wherein the cationic polymer is selected from the group consisting of chitosans, quaternized guar gums, and salts thereof.

3. The composition according to claim 2, wherein the cationic polymer is selected from the group consisting of chitosan glycolate, chitosan lactate, chitosan pyrrolidone carboxylic acid salt and chitosan monosuccinamide.

4. The composition of claim 1, comprising more than one said cationic polymer.

5. The composition according to claim 1, wherein the microparticles or nanoparticles are selected from the group consisting of microcapsules, microspheres, macromolecular complexes, nanospheres and nanocapsules.

6. The composition according to claim 1, wherein the microparticles or nanoparticles have a diameter between 0.01 and 150 $\mu$m.

7. The composition according to claim 1, wherein the microparticles or nanoparticles are obtained by a method in which a liquid crystal homogeneous lamellar phase is prepared which comprises at least one surfactant, at least one solvent and a biologically active substance which is to be encapsulated and which forms a stacking of membranes, and in which method the lamellar phase is subjected to a constant shearing.

8. The composition according to claim 1, comprising a plurality of active substances combined in said microparticles or nanoparticles.

9. The composition according to claim 1, wherein the micro or nanoparticles also comprise a cationic polymer.

10. The composition according to claim 1, further comprising an active molecule directly distributed in the vehicle.

11. A method of treating human or animal skin, comprising applying thereto a composition according to claim 1.

12. The method according to claim 11, which is a therapeutic, cosmetic or hygienic method of treatment of a human or animal body.

13. The composition according to claim 1, wherein the active sustance is an insecticide.

14. The composition according to claim 1, wherein the at least one active molecule is selected from the group consisting of natural molecules of plant origin, natural molecules of animal origin, natural molecules of mineral origin and synthetic molecules.

15. A method for improving activity of at least one biologically active substance selected from the group consisting of an antiseptic agent, an antibiotic agent, an antiviral agent, an antifungal agent, an antiparasitic agent, an insecticidal agent, an acaricidal agent and an antimitotic agent by increasing its activity and duration thereof which comprises combining, within a pharmaceutically or cosmetically acceptable medium said at least one said active substance contained in microparticles or nanoparticles which are approximately spherical multilamellar vesicles of onion structure, and at least one cationic polymer selected from the group consisting of cationic polysaccharides, the at least one cationic polymer being dispersed directly within the medium.

16. A composition for skin treatment, comprising:
a) a pharmaceutically or cosmetically acceptable medium;
b) dispersed directly within the medium, 0.001 to 5% by weight of the composition of at least one cationic polymer selected from the group consisting of cationic polysaccharides; and
c) dispersed within the medium, 0.5 to 50% by weight of the composition of microparticles or nanoparticles containing at least one biologically active molecule therein selected from the group consisting of an antiseptic, an antibiotic, an antiviral, an antifungal, an antiparasitic, an insecticidal, an acaricidal and an antimitotic for treating the skin, said microparticles or nanoparticles being approximately spherical multilamellar vesicles of onion structure, whereby the simultaneous presence of the at least one cationic polymer and the microparticles or nanoparticles in said composition improves the activity of the at least one active molecule by reducing time required for a desired antiseptic, antibiotic, antiviral, antifungal, antiparasitic, insecticidal, acaricidal, or antimitotic activity in comparison to a composition in which either the microparticles or nanoparticles of the cationic polymer, or both, are not present.

17. A composition for skin treatment, comprising:
a) a pharmaceutically or cosmetically acceptable medium;
b) dispersed directly within the medium, 0.001 to 5% by weight of the composition of at least one cationic polymer selected from the group consisting of cationic polysaccharides; and
c) dispersed within the medium, 0.5 to 50% by weight of the composition of microparticles or nanoparticles containing at least one biologically active molecule therein selected from the group consisting of an antiseptic, an antibiotic, an antiviral, an antifungal, an antiparasitic, an insecticidal, an acaricidal and an antimitotic for treating the skin, said microparticles or nanoparticles being approximately spherical multilamellar vesicles of onion structure, whereby the simultaneous presence of the at least one cationic polymer and the microparticles or nanoparticles in said composition improves the activity of the at least one active molecule by increasing duration of a desired antiseptic, antibiotic, antiviral, antifungal, antiparasitic, insecticidal, acaricidal, or antimitotic activity in comparison to a composition in which either the microparticles or nanoparticles of the cationic polymer, or both, are not present.

* * * * *